(12) United States Patent
Ueno et al.

(10) Patent No.: US 8,734,655 B2
(45) Date of Patent: May 27, 2014

(54) METHOD FOR REGENERATING FILTER

(75) Inventors: Koji Ueno, Hyogo (JP); Kunihiko Suzuki, Hyogo (JP); Atsushi Sugano, Hyogo (JP)

(73) Assignee: Nippon Shokubai Co., Ltd., Osaka (JP)

( * ) Notice: Subject to any disclaimer, the term of this patent is extended or adjusted under 35 U.S.C. 154(b) by 312 days.

(21) Appl. No.: 13/147,261

(22) PCT Filed: Jan. 26, 2010

(86) PCT No.: PCT/JP2010/050974
§ 371 (c)(1),
(2), (4) Date: Aug. 1, 2011

(87) PCT Pub. No.: WO2010/090100
PCT Pub. Date: Aug. 12, 2010

(65) Prior Publication Data
US 2011/0284470 A1    Nov. 24, 2011

(30) Foreign Application Priority Data

Feb. 3, 2009 (JP) .................................. 2009-022639

(51) Int. Cl.
*B01D 41/00* (2006.01)

(52) U.S. Cl.
USPC .......................................... 210/797; 134/29

(58) Field of Classification Search
USPC ............................... 210/797; 562/600; 134/29
See application file for complete search history.

(56) References Cited

U.S. PATENT DOCUMENTS

| 7,129,376 B2 * | 10/2006 | Hammon et al. ............. 562/600 |
| 2002/0121483 A1 | 9/2002 | Krulik |
| 2007/0173665 A1 | 7/2007 | Ueno et al. |
| 2007/0173666 A1 | 7/2007 | Ishii et al. |
| 2009/0124835 A1 | 5/2009 | Yamaguchi et al. |

FOREIGN PATENT DOCUMENTS

| JP | 62120341 A | 6/1987 |
| JP | 01307407 A | 12/1989 |
| JP | 09141058 A | 6/1997 |
| JP | 2002248325 A | 9/2002 |
| JP | 2007191449 A | 8/2007 |
| JP | 2007217403 A | 8/2007 |
| WO | 2007052505 A1 | 5/2007 |

OTHER PUBLICATIONS

Extended European Search Report issued Apr. 23, 2013.
Notification Concerning Transmittal of International Preliminary Report on Patentability (PCT/IB/338) and English Translation.
International Preliminary Report on Patentability (PCT/IB/373) and English Translation.
Written Opinion of the International Searching Authority (PCT/ISA/237) and English Translation.

* cited by examiner

*Primary Examiner* — Matthew O Savage
(74) *Attorney, Agent, or Firm* — Porzio, Bromberg & Newman, P.C.

(57) ABSTRACT

[PROBLEM] There is provided a method for regenerating a filter, by which deterioration of the color tone of purified acrylic acid can be prevented.
[SOLUTION] There is provided a method for regenerating a filter which has been used in a filtration step in the process for producing an acrylic acid, comprising a step (A) wherein the filter is washed with an aqueous alkaline solution, a step (B) wherein the filter is washed with water after the step (A), and a step (C) wherein the filter is brought into contact with the acrylic acid for regeneration for at least one hour after the step (B).

6 Claims, No Drawings

METHOD FOR REGENERATING FILTER

CROSS REFERENCE TO RELATED APPLICATIONS

This is a National Stage of International Application No. PCT/JP2010/050974, filed 26 Jan. 2010, which claims the benefit of Application No. 2009-022639, filed in Japan on 3 Feb. 2009, the disclosures of which Applications are incorporated by reference herein.

TECHNICAL FIELD

The present invention relates to a method for regenerating a filter, and it is particularly related to the method for regenerating a filter which has been used in a filtration step in the process for producing an acrylic acid.

BACKGROUND ART

The process for producing an acrylic acid via a catalytic gas phase oxidation process, an absorption and/or a condensation process, and further a distillation purification and/or a crystallization process has been industrially performed widely. Purified acrylic acid is transferred and stored in a storage tank, and if a trace of acrylic acid polymer is contained in the purified acrylic acid, an acrylic acid polymer will be further generated during storage, and problems such as the decreasing of purity of the purified acrylic acid are caused.

In order to solve the above problems, the present inventors have previously proposed a method for filtering with a filter when the purified acrylic acid is transferred to a storage tank. (Refer to patent document 1). In said method, in order to remove the acrylic acid polymer adhered to the used filter, the filter was washed with aqueous sodium hydroxide solution after water washing, and further water washing was carried out.

The acrylic acid polymer adhered on the filter can be substantially removed by washing with water and aqueous sodium hydroxide solution, and performing further water washing as described in the above patent document 1. It should be noted that a final water washing is performed for removing the alkaline residues which remain on the filter after washing with aqueous sodium hydroxide solution.

PRIOR ART REFERENCES

Patent Literatures

[Patent document 1] JP-A-2007-191449

SUMMARY OF INVENTION

Technical Problem

However, present inventors found that when the filter regenerated by the above methods was re-used for filtration of the purified acrylic acid, the color tone of the purified acrylic acid after restarting the filtration was bad, and the metal (mainly iron) content was high, and the metal had affected the color tone of the purified acrylic acid. Moreover, it was found that, by passing some amount of the purified acrylic acid through a filter, the color tone and metal content of the purified acrylic acid could return to APHA 5 or less and the metal content of 1 ppm by mass or less, which is the value in the purified acrylic acid immediately after a crystallization process and is the usual value generally required for the product acrylic acid. However, till the color tone and metal contents of the purified acrylic acid return to the usual value, it is necessary to passing a large amount of the acrylic acid for regeneration through the filter. As the result, the quantity of the off-specification product of acrylic acid increases. Although the acrylic acid, which is said off-specification product, may be recycled for a recovery step, another crystallization step, etc., the production cost of acrylic acid become expensive.

In recent years, because a high quality product of acrylic acid with a good color tone has been required, solution of the above problems is strongly desired. In addition, it is also desirable from the point of cost reduction to make the amount of off-specification product as less as possible.

From this viewpoint, it is an object of the present invention to provide a method for regenerating the filter which prevents the color tone of the purified acrylic acid from deteriorating.

Means for Solving the Problem

The present inventors have investigated in detail arid found that the above metal contained a metal (mainly iron) that was slightly eluted from the reactor used in the process for producing acrylic acid. That is, the metal remains on the filter as an oxide when the filter is washed with aqueous alkaline solution, and when said filter is re-used, the metal is eluted into the purified acrylic acid and causes a deterioration of the color tone of the purified acrylic acid. In order to resolve the above causes, the present inventors have intensively studied and completed this invention.

That is, the present invention is a method for regenerating a filter which has been used in a filtration step in the process for producing acrylic acid, comprising a step (A) wherein the filter is washed with an aqueous alkaline solution, a step (B) wherein the filter is washed with water after the step (A), and a step (C) wherein the filter is brought into contact with acrylic acid for regeneration for at least one hour after the step (B).

Advantageous Effect of the Invention

The present invention can prevent deterioration of the color tone of the purified acrylic acid.

DESCRIPTION OF THE PREFERRED EMBODIMENTS

Hereinafter, the preferred embodiments of the present invention is explained.

The present invention is a method for regenerating a filter which has been used in a filtration step in the process for producing acrylic acid, comprising a step (A) wherein the filter is washed with an aqueous alkaline solution, a step (B) wherein the filter is washed with water after the step (A), and a step (C) wherein the filter is brought into contact with acrylic acid for regeneration for at least one hour after the step (B).

The process for producing acrylic acid of the present invention is not particularly limited. For example, there is included a process which comprises of a process wherein acrylic acid is produced via a catalytic gas phase oxidation process, an absorption and/or a condensation process, and further distillation purification and/or crystallization process. It should be noted that a "crystallization process" is a well-known process for purifying acrylic acid by crystallizing, sweating and melting.

The filtering process of the present invention is performed in order to remove the acrylic acid polymer included in the purified acrylic acid, and it is performed with a filter. The filtering process will not be particularly limited as long as it is carried out in the process for producing the acrylic acid, but there is included the case where it is carried out when transferring the purified acrylic acid obtained from a distillation purification and/or crystallization process to storage tanks thereof, or the case where it is carried out when transferring to another storage tank installed as needed, before supplying the acrylic acid solution obtained from the absorption and/or condensation process to a distillation purification and/or crystallization process. Especially, it is preferable to be performed in the line during the transfer of the purified acrylic acid obtained from a crystallization process to a storage tank thereof.

The kind, shape or material etc. of the filter to be regenerated in the present invention is not especially limited, any one will be enough as long as it is able to be used to remove the acrylic acid polymer. Especially, a commercially available cartridge type filter is suitably employed for convenience of operation. Specifically, there are included a membrane cartridge filter made of polytetrafluoroethylene (PTFE), a pleats cartridge filter made of polypropylene (PP), a depth cartridge filter, a wound cartridge filter, and a pleats cartridge filter made of stainless steel etc. The present invention is especially effective in regeneration of a cartridge filter made of resin such as PTFE and PP, which cannot be reversely washed in terms of its strength.

As for the method for regenerating the filter, a filter housing that storing a cartridge-type filter is used alone, or two or more filter housing that storing a cartridge-type filter can be used in the any form disposed in tandem and/or in parallel. Preferably, two filter housing (I) and (II) are installed in parallel, and at first, the purified acrylic acid is flowed into filter housing (I) and then filtered. Then, if the differential pressure onto a filter .increases due to adhesion of the polymer onto the filter, the flow of the purified acrylic acid will be changed to filter housing (II), and filtration of the purified acrylic acid will be continued. The filter in the above filter housing (I) is regenerated, for example, as follows, though it is not especially limited to the following order 1) The acrylic acid which remained in the housing is removed and recovered.
2) The inside of the housing is washed with water, and the residual acrylic acid is flushed out [a step (X)].
3) An aqueous alkaline solution is filled in the housing and the polymer adhered to the filter is removed [a step (A)].
4) After the aqueous alkaline solution is removed from the housing, the inside of the housing is washed with water, and the alkaline is flushed out [a step (B)].
5) The inside of the housing is filled with the acrylic acid for regeneration, and a filter is brought in contact with the said acrylic acid [a step (C)].

The above step 1) may be a general removal and a recovery, for example, flushing out is included. The recovered acrylic acid can be circulated to the absorbing step of acrylic acid.

In the above step 2), the pH of water after flushing out the residual acrylic acid is preferably 4.0 or more, and more preferably, the washing is repeated and flushed out until the pH becomes 5.5 or more, further more preferably 6.5 or more.

In the above step 3), an aqueous lithium hydroxide solution, an aqueous sodium hydroxide solution, an aqueous magnesium hydroxide solution, an aqueous potassium hydroxide solution, an aqueous calcium hydroxide solution, an aqueous barium hydroxide solution etc., can be used as the "aqueous alkaline solution", the aqueous sodium hydroxide solution and the aqueous potassium hydroxide solution are preferable from the viewpoint of ready availability and removal capability of the polymers. The concentration of the aqueous alkaline solution is not particularly limited, but preferably 0.1 to 30% by mass, more preferably 1.0 to 20% by mass, and further more preferably 2.0 to 15% by mass. Usually, said alkaline solution is circulated in the housing and promotes removal of the polymer adhered to the filter.

In the above step 4), the pH of water after flushing out the residual alkali is preferably 8.0 or less, and more preferably, the washing is repeated and flushed out until the pH becomes 7.5 or less.

In the above step 5), the filter may be brought in contact with the acrylic acid for regeneration, and the contact method is not particularly limited. For example, the acrylic acid for regeneration is poured from the upper part of the filter, or the filter is immersed into the acrylic acid for regeneration, etc. When the filter is immersed in the acrylic acid for regeneration, it is only permitted to immerse in stationary acrylic acid for regeneration or in some case, to immerse in circulated acrylic acid for regeneration. Furthermore, at a given point in contacting with the acrylic acid for regeneration, mechanical method such as rubbing off may be added. It is desirable that the above acrylic acid for regeneration has a purity which can wash efficiently the filter, and the APHA of the acrylic acid for regeneration is preferably 10 or less, more preferably 5 or less, and further more preferably 2 or less. Furthermore, the metal content of the acrylic acid for regeneration is preferably 3 ppm by mass or less, more preferably 1 ppm by mass or less, and further more preferably 0.1 ppm by mass or less. In addition, the temperature of the acrylic acid for regeneration is in the range of 14 to 80° C. in consideration of the melting point of acrylic acid and the heat resistance-temperature of the filter etc., and more preferably 15 to 40° C. in consideration of the polymerizability of the acrylic acid.

The time during which a filter is brought in contact with the acrylic acid for regeneration under the above condition, is preferably at least 1 hour or more, and more preferably 2 hours or more. When the filter is immersed in acrylic acid for regeneration for 1 hour or more, metal oxides on the filter can be fully removed and the amount of the above-mentioned off-specification product decreases.

By using the filter after performed the above steps 1 to 5 for the filtering step, deterioration of the color tone of the purified acrylic acid can be prevented efficiently.

The above regeneration of the filter may be performed out of the housing by removing the filter. In addition, filter after regeneration can be used for a filtering step as is, without performing further operation, and can continue the production of acrylic acid efficiently.

EXAMPLE

Hereinafter, the present invention is explained still more specifically using examples and comparative examples. However, the technical range of the present invention is not necessarily restricted only to the following examples, The color tone and the metal content (since the metal is mainly iron, the iron content is described) were measured by the following methods.

Color tone: Absorption colorimeter ("ColorPlus" of Color grade meter manufactured by SIGRIST-PHOTOMETER AG) was installed in the liquid sending line, and Hazen color number (API-IA) was measured online (wavelength at measurement, 365 nm; wavelength at comparison, 650 nm).

Iron contents : After diluting the acrylic acid with ultrapure water by 5 times, the sample was analyzed with an ICP (Inductively Coupled Plasma) Atomic Emission Spectrometer.

The purified acrylic acid used here was prepared as follows.

<Step of Absorbing Acrylic Acid>

The reactive gas obtained by a catalytic gas phase oxidation reaction of propylene by the same method as in the case of Example 1 of JP-A-2005-15478 was contacted with the aqueous solution for absorbing, and from the bottom of the absorption column, an acrylic acid solution with a composition of acrylic acid 90.0% by mass, water 3.2% by mass, acetic acid 1.9% by mass, maleic acid 0.6% by mass, acrylic acid dimer 1.5% by mass, aldehydes 0.4% by mass , hydroquinone 0.1% by mass, and other impurities 2.3% by mass was obtained. It should be noted that the temperature at the bottom of absorption column at this time, i.e., the temperature of the acrylic acid solution removed from the absorption column, was 91° C.

<Step of Crystallization of Acrylic Acid>

After cooling the above acrylic acid solution, it was supplied to a crystallizer, and dynamic crystallization was repeated 4 times to purify. Dynamic crystallization was performed using the crystallizer according to the crystallizer described in JP-B-53-41637. That is, an apparatus which is equipped with a reservoir in the lower portion and enables a liquid in the reservoir to transfer in a metal tube having a length of 6 m and an inner diameter of 70 mm by use of a circulation pump to the upper part of the tube and to flow along the inner wall surface of the tube as falling film is used. The surface of the tube is composed of a double jacket and the jacket is controlled so as to be a constant temperature by use of a thermostat. A cycle of dynamic crystallization was performed according to the following procedures.

1) Crystallization: the crude acrylic acid was supplied to the reservoir, flowed along of the inner wall surface of the tube as falling film by a circulation pump, and the jacket temperature was reduced below the freezing point, to crystallize about 60 to 90% by mass of acrylic acid on the wall surface.
2) Sweating: the circulation pump was stopped, and the jacket temperature was raised to near the freezing point, and about 2 to 20% of the acrylic acid crystal was sweated. After sweating, residual melted liquid was pumped out with the pump.
3) Melting: the jacket temperature was raised to the freezing point or more, and the crystal was melted and then pumped out with the pump.

In the above operations, the temperature and freezing point depend on each process carried out.

By the above, the purified acrylic acid having a purity of 99.93% by mass was obtained. Composition of other elements in said purified acrylic acid was water 100 ppm by mass, acetic acid 475 ppm by mass, maleic acid 2 ppm by mass, acrylic acid dimer 30 ppm by mass, and the aldehydes 0.4 ppm by mass. It should be noted that methoquinone was added to said purified acrylic acid as a stabilizer so as to be 200 ppm by mass.

The APHA value of the above purified acrylic acid was 2, and the iron content was 0.1 ppm by mass The above purified acrylic acid was passed into the cartridge housing which stored the cartridge filter (TCP-1 manufactured by ADVANTEC, a pleats cartridge filter made of PP, pore size with 1 μm) , and it was supplied to the storage tank. The linear velocity of the purified acrylic acid in the filter part at this time was 0.01 m/s.

When the differential pressure in the filter part became 0.1 MPa, the supply of the purified acrylic acid was stopped, and the filter was regenerated with the following procedures.

Example 1

1) The acrylic acid which remained in the housing was removed. Said acrylic acid was recovered and was circulated to the absorbing step for acrylic acid.
2) Water was supplied to the housing and water washing of the filter was performed. That is, after filling the interior of the housing with water, continual operation of removing water immediately was repeated until the pH of the water after washing became 6.5. Part of the washing water in the early stage of washing was circulated to the above-mentioned absorbing step for acrylic acid after recovery, and the subsequent residual washing water was removed from the system.
3) Aqueous sodium hydroxide solution 10 mass % was supplied to the housing, and alkaline washing of the filter was performed. The alkaline washing was performed as follows. That is, after filling the housing with aqueous sodium hydroxide solution and circulating this aqueous sodium hydroxide solution inside the housing for a while with a pump, the aqueous alkaline solution was removed from housing. Such operations were repeated 3 times. The aqueous alkaline solution. after washing was removed from the system.
4) Water was supplied in the housing and water washing of a filter was performed. That is, after filling the housing with water, continuous operation of removing the water immediately was repeated until the pH of the liquid after washing became 7.5.
5) Purified acrylic acid was supplied in the housing as acrylic acid for regeneration, and the housing was filled with said acrylic acid. After the filter was immersed for 1 hour, holding the temperature of the above-mentioned acrylic acid for regeneration at 40° C., said acrylic acid was removed. The removed acrylic acid was recovered and circulated to the above-mentioned crystallization process for acrylic acid.

After regenerating the filter by the above-mentioned procedure, the supply of the purified acrylic acid to this filter was restarted. The color tone of the acrylic acid which flowed out of the filter immediately after the restart was 5 (APRA) , and the iron content was 1.3 ppm by mass. Two hours afterward, the color tone became 2 (APHA) , the iron content became 0.1 ppm by mass, and returned to the initial value of the purified acrylic acid. Then, the supply of the filtered acrylic acid to the storage tank was started. Acrylic acid between the restarting of filtration and the time when the color tone and the iron content returned to the initial levels of the purified acrylic acid was recovered as an off-spec product, and it was then circulated to the above-mentioned crystallization process. Accordingly, a step of filtering acrylic acid with the regenerated filter to produce filtered acrylic acid that is collected separately from the acrylic acid used to regenerated the filter is carried out.

Example 2

A procedure similar to that in Example 1 was carried out except that the temperature of the acrylic acid for regeneration was 25° C. in the above-mentioned step 5).

Example 3

A procedure similar to that in Example 1 was carried out except that the temperature of the acrylic acid for regeneration was 15° C. in the above-mentioned step 5).

Example 4

A procedure similar to that in Example 2 was carried out except that the immersion time in the acrylic acid for regeneration was 2 hrs in the above-mentioned step 5).

Example 5

A procedure similar to that in Example 2 was carried out except that the immersion time in the acrylic acid for regeneration was 3 hrs in the above-mentioned step 5).

Example 6

A procedure similar to that in Example 2 was carried out except that the immersion time in the acrylic acid for regeneration was 6 hrs in the above-mentioned step 5).

Example 7

A procedure similar to that in Example 2 was carried out except that the immersion time in the acrylic acid for regeneration was 9 hrs in the above-mentioned step 5).

Example 8

A procedure similar to that in Example 2 was carried out except that the immersion time in the acrylic acid for regeneration was 12 hrs in the above-mentioned step 5).

Comparative Example 1

A procedure similar to that in Example 2 was carried out except that the acrylic acid for regeneration was not filled in the above-mentioned step 5).

Comparative Example 2

A procedure similar to that in Example 2 was carried out except that the immersion time in the acrylic acid for regeneration. was 0.5 hrs in the above-mentioned step 5).

Comparative Example 3

A procedure similar to that in Example 1 was carried out except that the immersion time in the acrylic acid for regeneration was 0.5 hrs in the above-mentioned step 5).

Comparative Example 4

A procedure similar to that in Example 3 was carried out except that the immersion time in the acrylic acid for generation was 0.5 hrs in the above-mentioned step 5).

The above result is shown in Table 1. It should be noted that the "Required time" in Table 1 means the following total time; after restarting filtration with a regenerated filter, until the color tone and the metal content of the filtered acrylic acid reaches the initial color tone (APHA 2) and metal content (mainly, the iron content) (0.1 ppm by mass) of the purified acrylic acid, and then it becomes possible to transfer this product to storage tanks.

TABLE 1

| | Immersion time (hr) | Temperature of acrylic acid for regeneration (° C.) | Quality immediately after restart APHA | Iron content (ppm) | Required time (hr) |
|---|---|---|---|---|---|
| Example 1 | 1 | 40 | 5 | 1.3 | 2.0 |
| Example 2 | 1 | 25 | 8 | 2.4 | 3.7 |
| Example 3 | 1 | 15 | 9 | 3.0 | 4.6 |
| Example 4 | 2 | 25 | 6 | 1.5 | 2.4 |
| Example 5 | 3 | 25 | 5 | 1.2 | 1.8 |
| Example 6 | 6 | 25 | 4 | 0.6 | 1.0 |
| Example 7 | 9 | 25 | 3 | 0.3 | 0.5 |
| Example 8 | 12 | 25 | 2 | 0.2 | 0.25 |
| Comparative example 1 | — | 25 | 22 | 8.0 | 12.5 |
| Comparative example 2 | 0.5 | 25 | 19 | 6.8 | 10.6 |
| Comparative example 3 | 0.5 | 40 | 18 | 6.6 | 10.3 |
| Comparative example 4 | 0.5 | 15 | 19 | 6.9 | 10.8 |

From Table 1, it is understood that when the temperature of the acrylic acid for regeneration employed for immersion is higher, and/or the immersion time in this acrylic acid is longer, the quality immediately after the restart is preferable, and the required time is shortened.

The invention claimed is:

1. A method for regenerating a used filter which has been used in a filtration step in the process for producing an acrylic acid, comprising:
    washing the used filter with an aqueous alkaline solution;
    washing the used filter with water after the step of washing the used filter with an aqueous alkaline solution;
    contacting the used filter with acrylic acid for at least one hour after the step of washing the used filter with water to regenerate the used filter; and
    filtering acrylic acid with the regenerated filter to produce filtered acrylic acid that is collected separately from the acrylic acid used to regenerate the filter.

2. The method for regenerating according to claim 1, wherein a temperature of the acrylic acid for regeneration is from 14 to 80° C.

3. The method for regenerating according to claim 1, wherein the the step of contacting the used filter with acrylic acid is made by immersion of the used filter into acrylic acid.

4. The method for regenerating according to claim 1, wherein the filter is a cartridge filter.

5. The method for regenerating according to claim 1, wherein a step of water-washing of the filter is further included before the step of washing the used filter with an aqueous alkaline solution.

6. The method for regenerating according to claim 1, wherein the filtration step is performed in a line where the purified acrylic acid, obtained in a crystallization process for producing the acrylic acid, is transferred to a storage tank.

* * * * *